(12) United States Patent
Mao

(10) Patent No.: US 6,423,229 B1
(45) Date of Patent: Jul. 23, 2002

(54) BIOREACTOR SYSTEMS FOR BIOLOGICAL NUTRIENT REMOVAL

(75) Inventor: Huazhong Mao, Edmonton (CA)

(73) Assignee: Aquasol Envirotech Ltd., Vancouver (CA)

( * ) Notice: Subject to any disclaimer, the term of this patent is extended or adjusted under 35 U.S.C. 154(b) by 0 days.

(21) Appl. No.: 09/459,945

(22) Filed: Dec. 14, 1999

(51) Int. Cl.⁷ .................................................. C02F 3/00
(52) U.S. Cl. ...................... 210/603; 210/605; 210/606
(58) Field of Search ............................... 210/610, 605, 210/603, 630, 620–622, 606

(56) References Cited

U.S. PATENT DOCUMENTS

| 5,071,747 A | 12/1991 | Hough et al. |
| 5,240,598 A | 8/1993 | Portier et al. |
| 5,342,522 A | 8/1994 | Marsman et al. |
| 5,393,427 A | 2/1995 | Bernard |
| 5,534,143 A | 7/1996 | Portier et al. |
| 5,582,732 A | 12/1996 | Mao et al. |
| 5,853,588 A | 12/1998 | Molof et al. |
| 5,919,367 A | * 7/1999 | Khudenko |
| 6,015,496 A | * 1/2000 | Khudenko |

FOREIGN PATENT DOCUMENTS

JP 2000254675 A * 9/2000

OTHER PUBLICATIONS

US Trademark Electronic Search System (TESS) copy of US Trademark Registration No. 0390506 for TWEEN covering emulsifying, wetting and dispersing agents.*

* cited by examiner

Primary Examiner—Chester T. Barry

(57) ABSTRACT

An integrated biological treatment process and bioreactor system provides means for simultaneous removal of biodegradable solids (TSS), nitrogen (N) and phosphate (P) from water and wastewater. The system comprises microbial consortia immobilized in separate bioreactors for anaerobic processes, P removal, dentrification and, optionally, BOD removal and polishing.

19 Claims, 15 Drawing Sheets

Figure 1. Process Flow Diagram

FIGURE 2. PROCESS DIAGRAM AND BIOREACTOR SYSTEMS

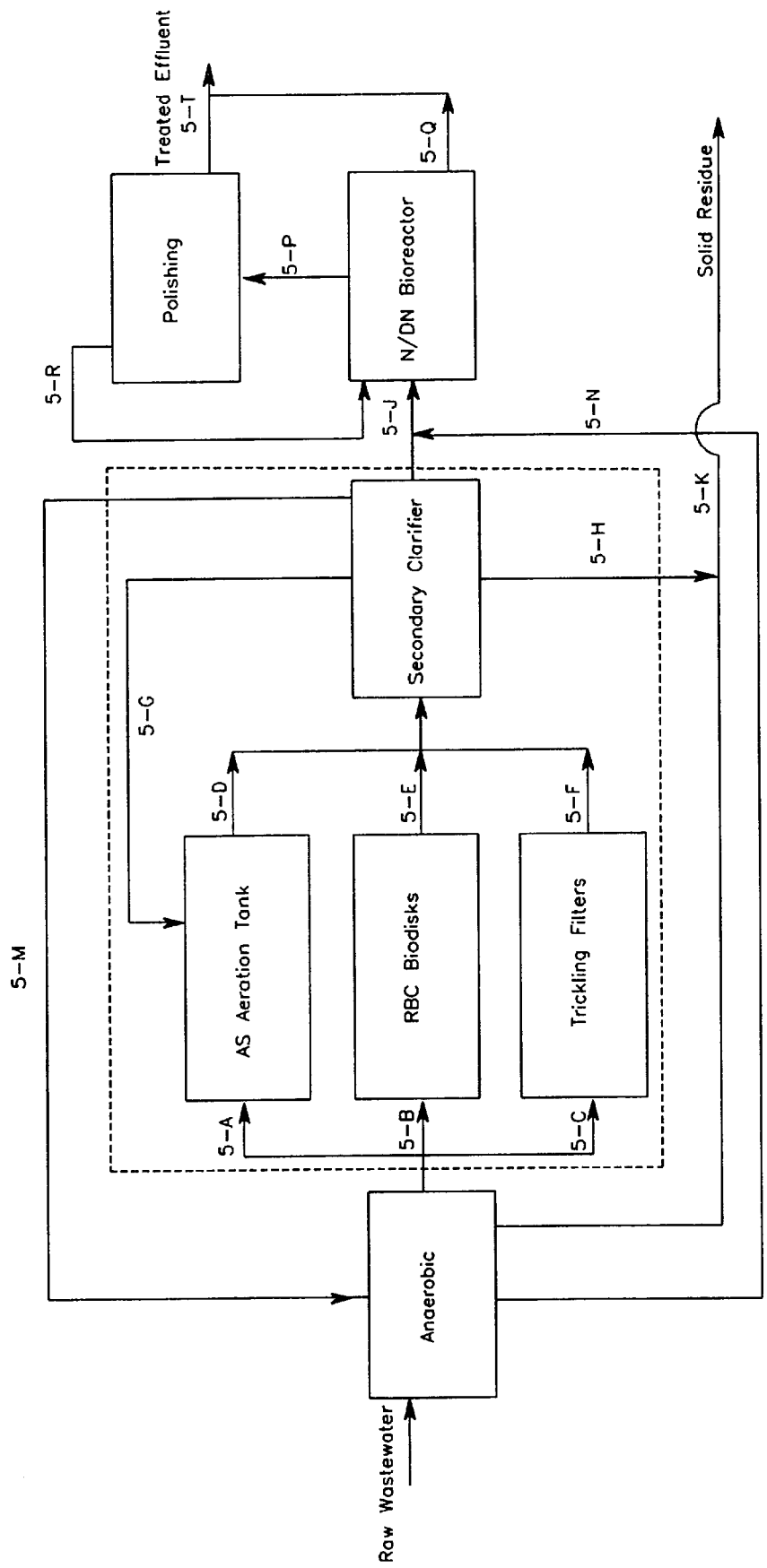
Figure 5 Process Diagram for Retrofitting Immobilized Living Cell Bioreactor Systems

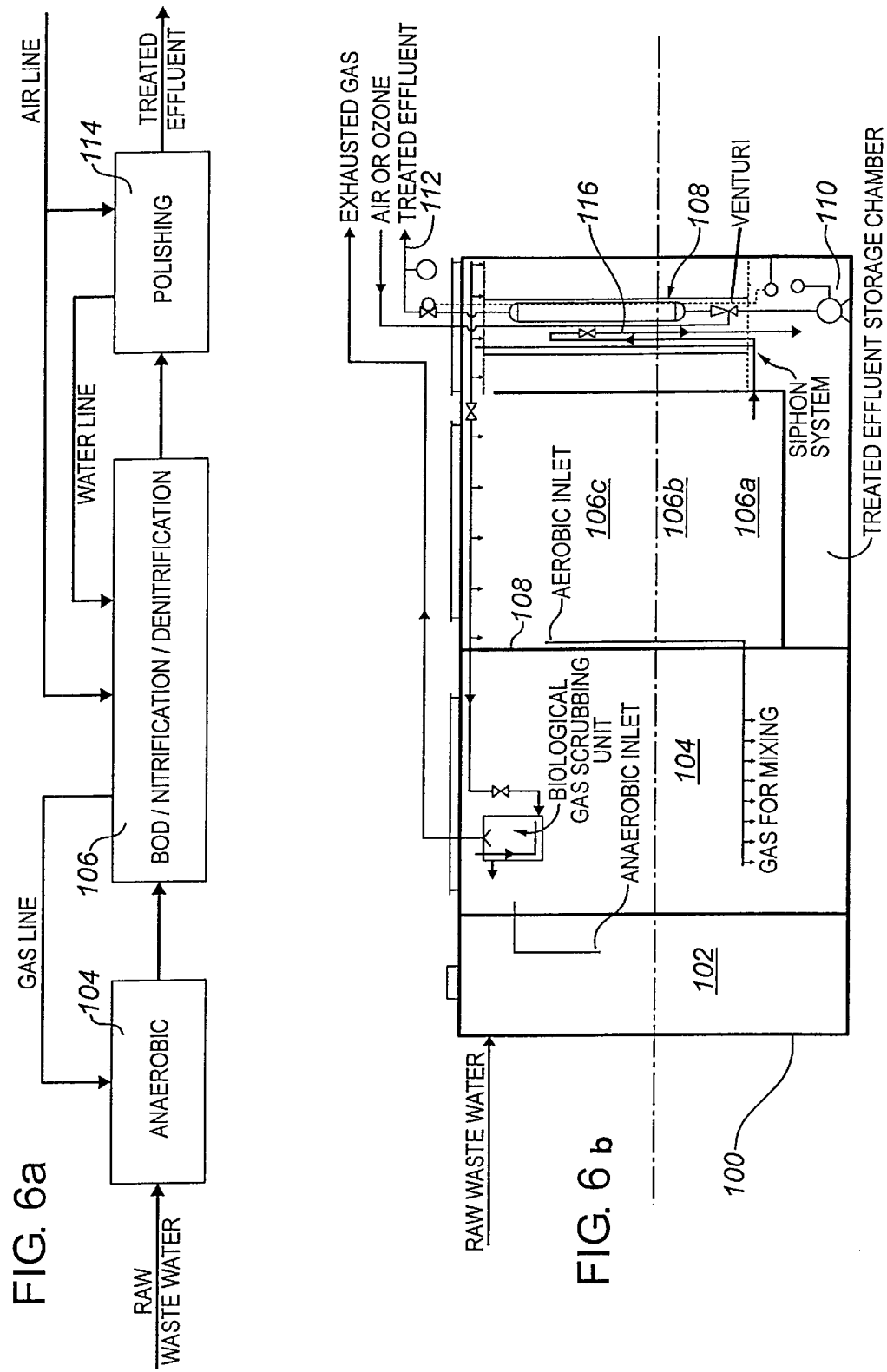

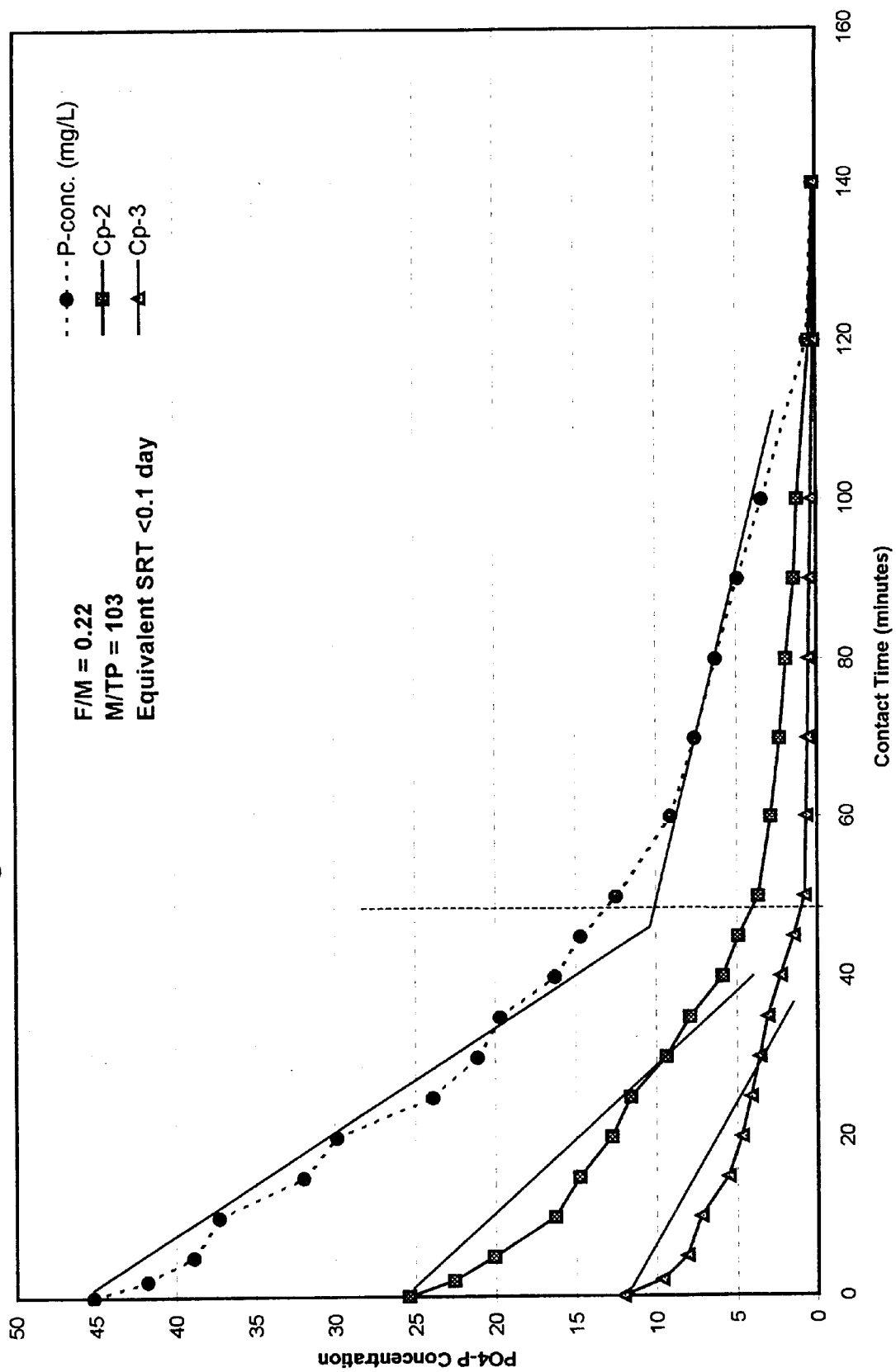
Figure 9. Biokinetics of P-removal

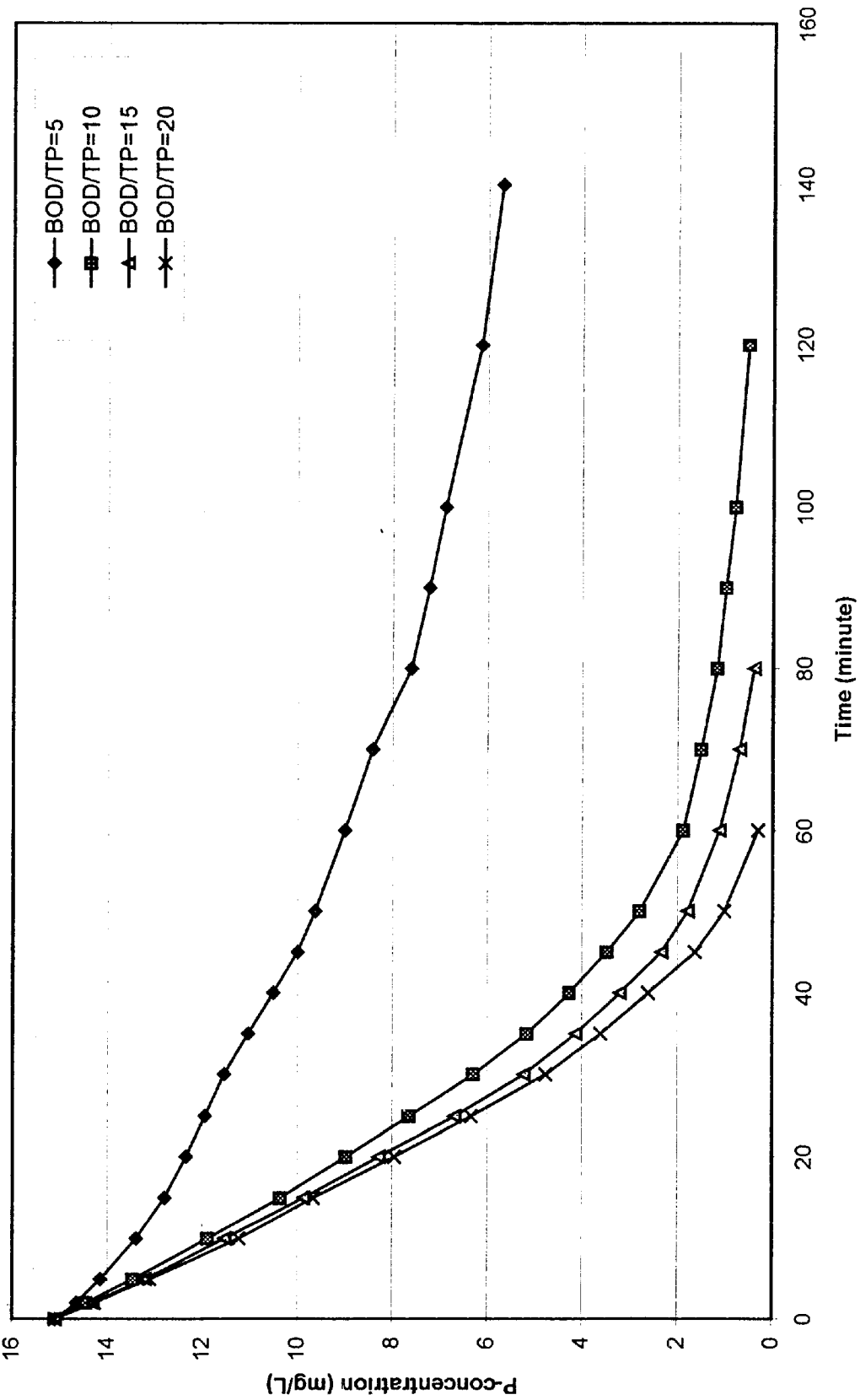

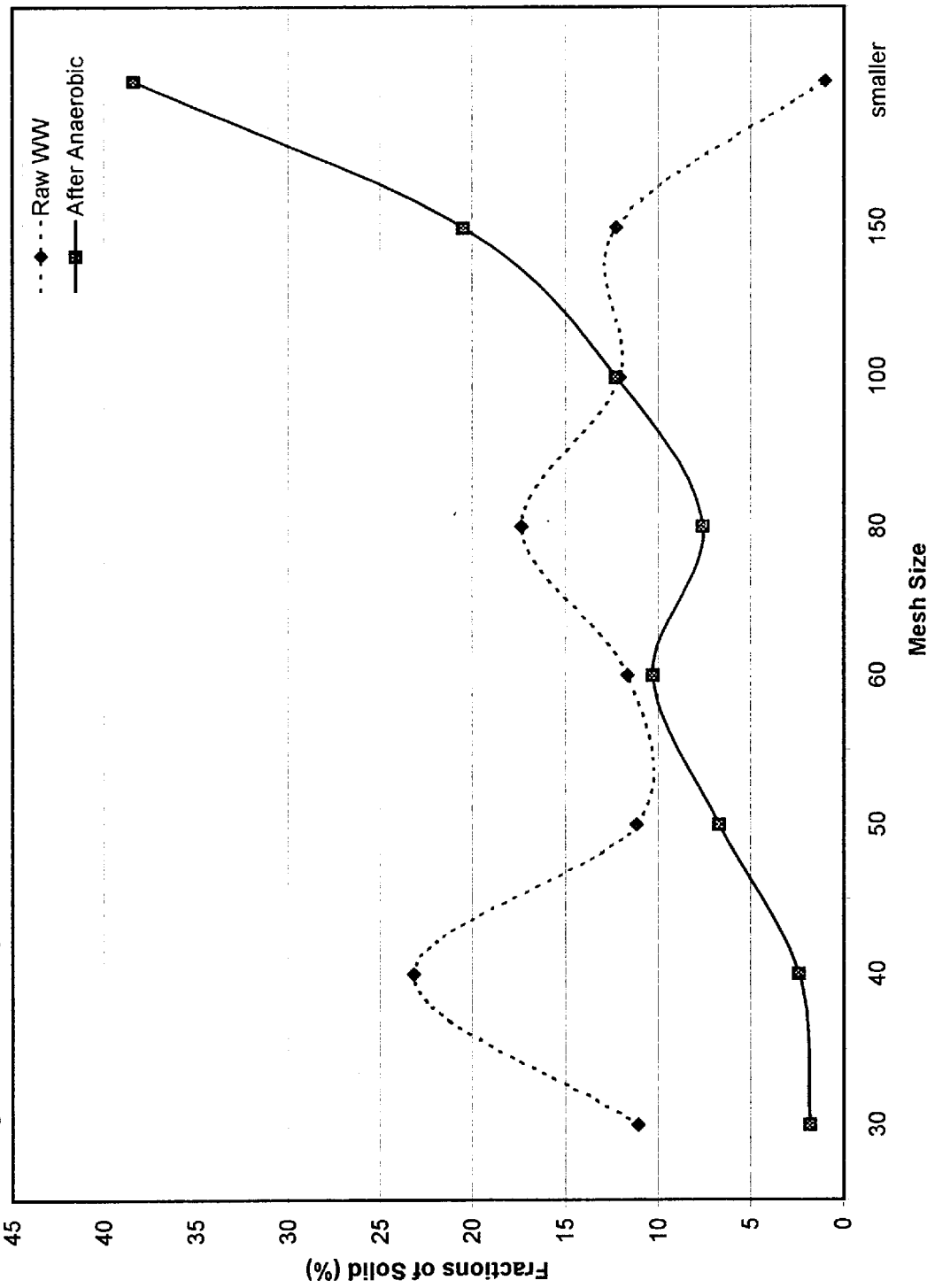

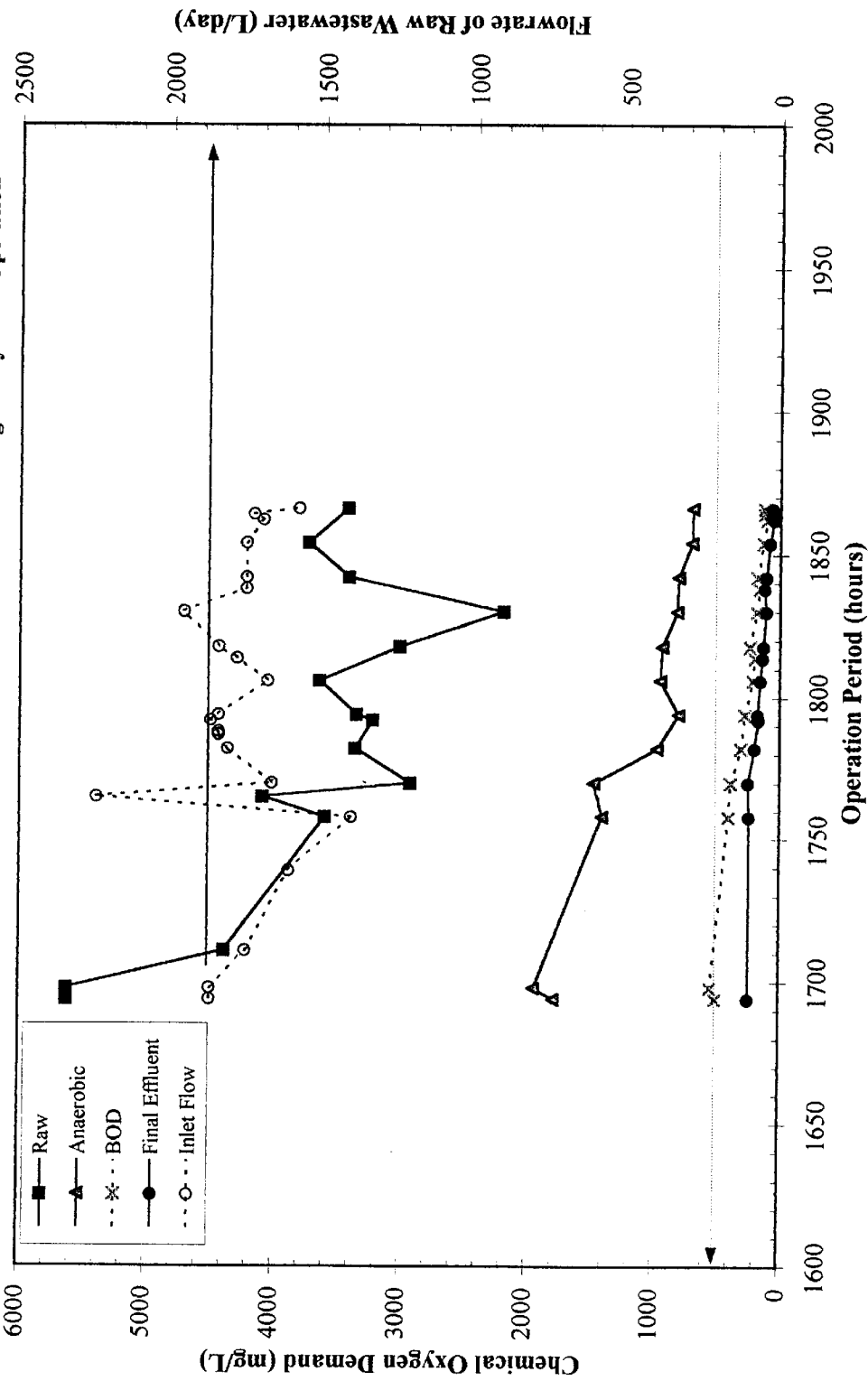
Figure 12. COD Reduction through Various Immobilized Bioreactor during Steady State Operation

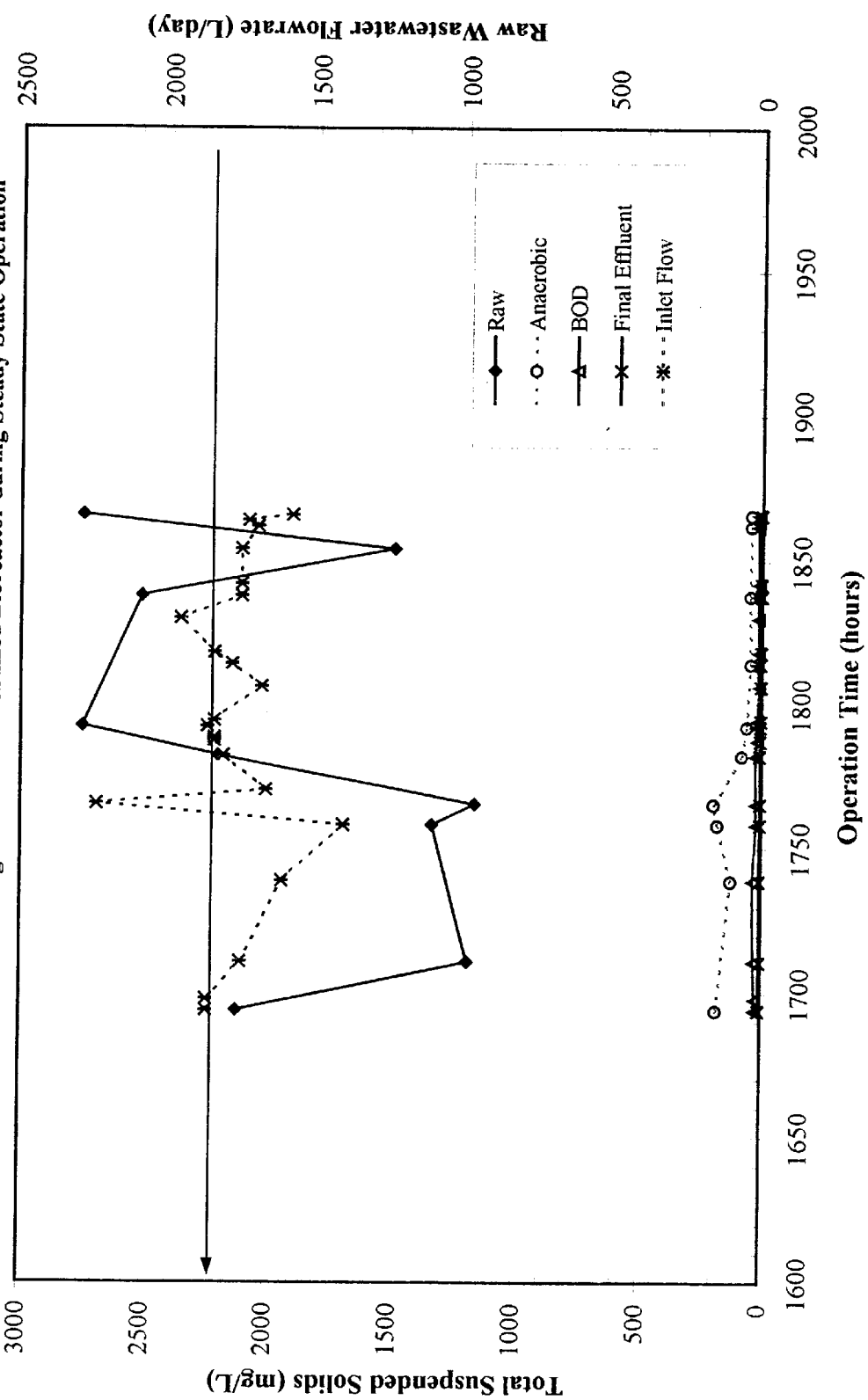
Figure 13. TSS Reduction through Various Immobilized Bioreactor during Steady State Operation

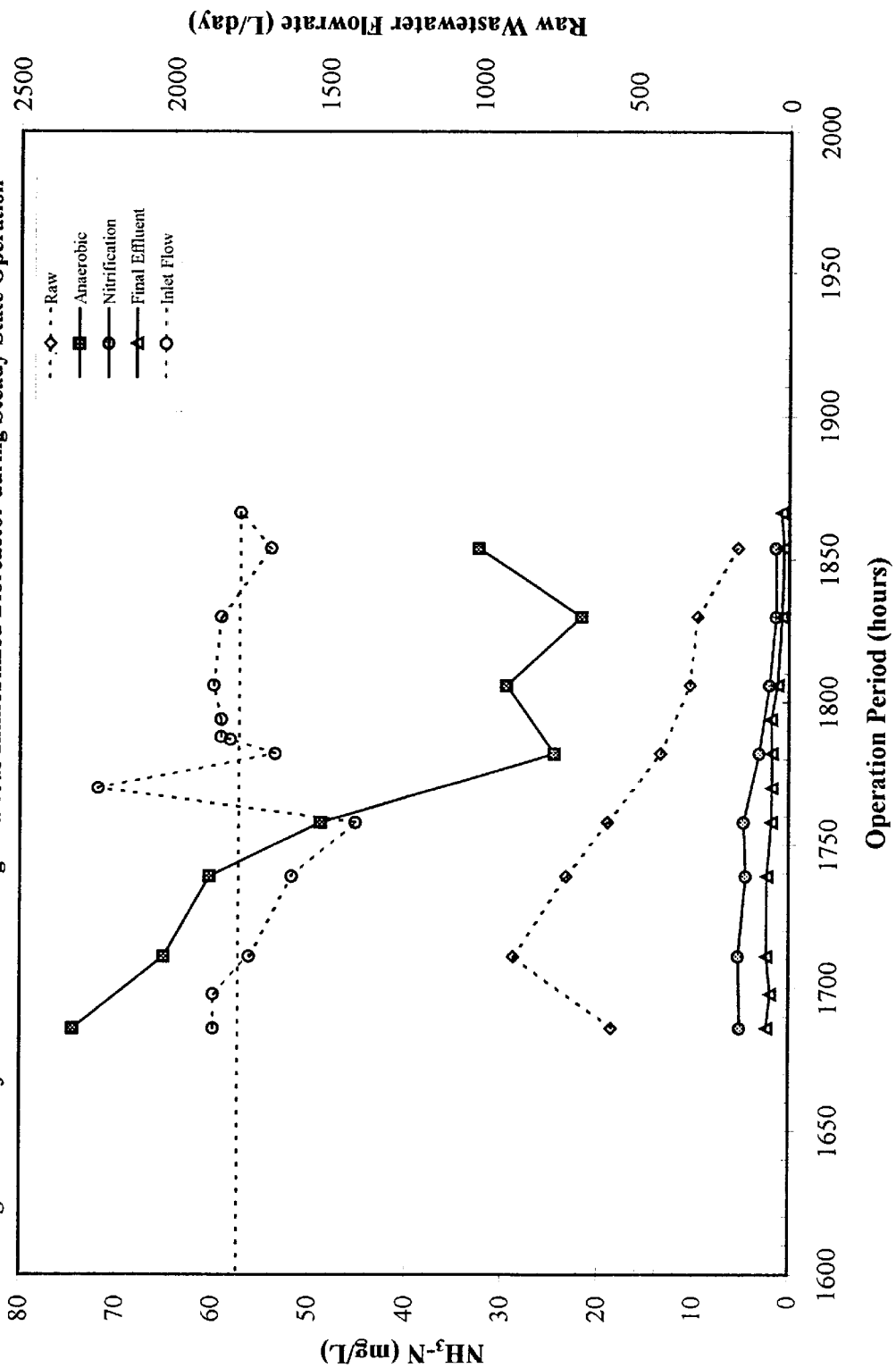
Figure 14. NH$_3$-N Reduction through Various Immobilized Bioreactor during Steady State Operation

BIOREACTOR SYSTEMS FOR BIOLOGICAL NUTRIENT REMOVAL

TECHNICAL FIELD

This invention relates to new methods and apparatuses for purification of water and wastewater with immobilized living cell bioreactor systems. In particular, the bioreactor systems may remove organic impurities, nitrogen, phosphorus and biodegradable solids.

BACKGROUND ART

In general, a biological wastewater treatment system usually consists of three essential components:

1. Living biomass

A wide variety of microorganisms have been found to remove different target pollutants. In order to maximize the efficiency of the biological treatment, it is necessary to select proper microbes depending on the types of pollutants to be treated. The acclimatization of microbial consortia for particular purposes is well known in the art. Some microbial species which have been characterized are available from recognized depositories of biological materials.

2. Biomass handling

A bioreactor may achieve high efficiency when it supports the living biomass to grow healthily in high density and retain them properly in the bioreactor under various adverse conditions. Biomass handling methods that are used in water and wastewater treatment may be generally classified into two general categories: suspended and immobilized biomass.

Suspended biomass systems have been widely used in activated sludge ("AS") systems and part of rotating biological contactor ("RBC") systems, however, the inherent limitations in these systems have driven continuous research in immobilized biomass methodology. Immobilization of living microbial cells as a means of handling biomass has gained increasing application, especially for biological nutrient removal.

Two predominant immobilization methods are a 'biofilm', in which the microorganisms are attached to solid surfaces, and an 'entrapped biomass', in which the microorganisms are held within micropores in the support material. The attached biofilm has been widely used in RBCs and trickling filters. In this method, the biomass is immobilized through adsorption and interactions between the microbial cells and the surfaces of supporting material. The immobilization of biomass using this method may be relatively weak, and the biomass periodically sloughs off the surface of the supporting material. Entrapment methods include the use of a matrix of calcium alginate gel. The major limitations of this immobilization method are that it is impractical to use in a commercial scale, as the beads are expensive and are mechanically or chemically instable. Poor mass transfer within the beads also greatly limits its application in large scale.

A porous ceramic immobilization material has been developed for large-scale applications. However, in practice, it has been found that the total suspended solids ("TSS") and the growth of microbial cells easily clog the micropores. As the micropores became clogged, mass transfer and headloss problems occur, similar to problems which affect calcium alginate gel systems, and only a thin layer of biofilm can grow on the surface of the ceramic immobilization material.

3. Hydraulics and mass transfer

A wastewater treatment system is only effective if the living biomass is provided with sufficient metabolic substrates and the waste metabolites are removed properly from the living biomass.

Obviously, the performance, flexibility and reliability of a biological wastewater treatment system are strongly dependent upon the effectiveness of the three components mentioned above. The main types of biological systems in wide use today, activated sludge (AS), rotating biological contactor (RBC) and conventional biofilters (or trickling filters) referred to above, suffer from shortcomings in one or more components mentioned above, which have been well documented in the literature.

Conventional biological wastewater treatment systems typically require a primary clarifier or sedimentation step, including the application of flocculating or coagulating chemicals, prior to biotreatment in order to mitigate the shortcomings of the prior art. This step is conventionally necessary to reduce the level of suspended solids so the biotreatment system does not become overloaded or clogged.

The biological conversion of complex or insoluble compounds containing phosphorus (P) nitrogen (N) into simply P or N, requires a series of biochemical reactions carried out by several different microbial consortia. These organisms grow under different conditions, have substantially different growth rates, and therefore compete differently for substrates, carbon and energy sources. Thus, any biological treatment system will only be effective if it can grow different desired microbial consortia, each to a high density and in a favorable environment.

Both phosphorus and nitrogenous compounds are encountered in wastewater in two general forms—inorganic and organic forms, which together make up total phosphorus (TP) or total nitrogen (TN). Complex phosphorus and nitrogenous compounds are found in soluble and insoluble states, and usually need to be converted into simple form such as orthophosphate or ammonia before use by most microorganisms.

Facultative anaerobic processes are found to be most effective for converting complex P or N into orthophosphate or ammonia. These processes involves various hydrolyzing enzymes from acclimatized microorganisms. However, these type of microorganisms usually grow slowly, are less competitive than other microorganisms and require certain special conditions.

After biological conversion, most of the N and P are in solution, and only a portion is assimilated into the biomass. Often, the ultimate goal is to reduce the N and P compounds from the water and wastewater to specified levels to meet discharge or re-use requirements. Several biological processes for removal of the N or P compounds are well known in the art. Such conventional systems typically involve suspended growth systems or sludge wasting methods.

To biologically remove soluble P, there is need for a selection system that allows for growth and retention of the P-removal microbial consortia in the bioreactor system in a reasonable concentration. This biomass may then absorb the $PO_4$-P in relatively high concentrations in its microbial cells. After reaching the maximum capacity under favorable conditions, the biomass is typically removed from the system and disposed of as waste sludge before it can release the absorbed P into the solution again. Although this treatment method may remove $PO_4$-P, the P removal biomass in the process varies considerably with the wastewater characteristics and operation, and it is very difficult to control. The disposal of significant amount of wasted biomass, or sludge, is also a great burden.

The chemistry of nitrogen is more complex because N can exist in seven oxidation states. Although many species of bacteria are able to change the oxidation states of N, they usually grow slowly and are much less competitive compared to heterotrophs. In addition, the biochemical processes for conversion of N are usually kinetic limiting processes. To improve the efficiency of these biological processes, it is desirable to selectively grow the desired species efficiently and in high density in the bioreactor and it is further desirable to provide the favorable growth conditions for these microorganisms to maximize N removal efficiency.

SUMMARY OF INVENTION

The present invention comprises integrated biological processes and novel bioreactor systems. In particular, this invention comprises a series of bioreactor systems using integrated biotreatment processes for the removal of organic material or BOD, suspended solids ("SS or TSS"), N and P from water and wastewater.

In general terms, the invention comprises a method of treating water or wastewater which involves first a facultative anaerobic process to degrade solids, break down complex compounds and produce simpler forms of P and N compounds, primarily phosphate and ammonia, as well as volatile fatty acids ("VFA's"). The VFA's are then contacted with a P-removal microbial consortia which uptakes and stores the VFA's anaerobically. The effluent is then passed to a nitrogen removal step where nitrate and ammonia are removed in an anoxic denitrification/aerobic nitrification bioreactor. As well, BOD may be substantially reduced at this stage. The effluent then returns to the P-removal bioreactor for aerobic phosphate removal. The effluent is now substantially free of N and P compounds as well as being substantially free of SS and BOD.

Therefore, in one aspect of the invention, the invention comprises a process of treating liquid contaminated with organic, BOD, COD, N containing and/or P containing compounds, said process comprising the steps of:

(a) passing the liquid through a P-removal bioreactor comprising an immobilized microbial consortia which are charged or recharged with a carbon source present in the liquid;

(b) passing the effluent from step (a) through the P-removal bioreactor which has been charged or recharged from step (a) under conditions which allow the microbial consortia to uptake and store P compounds;

(c) removing the wastewater from the P-removal bioreactor and providing a P-release solution effective to cause the microbial consortia to release the P previously stored; and (d) removing the P-release solution containing the released P from the P-removal bioreactor.

In one embodiment, the process of claim 1 further comprising the step of passing the liquid through an anaerobic bioreactor comprising an immobilized microbial consortia which degrade organic components in the liquid and produce volatile fatty acids which serves as the carbon source. The process may further comprise the step of passing the effluent from the P-removal bioreactor through at least one other bioreactor comprising an immobilized microbial consortia for at least partially removing N containing compounds, BOD and/or COD from the wastewater. The at least one other bioreactor may comprise a nitrogen removal bioreactor comprising a denitrification zone comprising microbial consortia which convert nitrogen oxides into nitrogen gas and a nitrification zone comprising microbial consortia which convert ammonia into nitrogen oxides. The at least one other bioreactor may further comprise an aerobic BOD removal bioreactor and/or an aerobic polishing bioreactor wherein residual ammonia and/or suspended solids are further polished out.

In one preferred embodiment, there are at least two P-removal bioreactors used alternately such that while one is being charged or recharged with effluent from the anaerobic bioreactor, one other is being used to treat effluent from the nitrogen removal bioreactor. More preferably, there are three P-removal bioreactors used alternately in a continuous fashion such that while one is being charged or recharged with effluent from the anaerobic bioreactor, a second is being used to treat effluent from the nitrogen removal bioreactor and the third is being treated with the P-release agent.

In another embodiment, the process further comprises a step of passing at least a portion of the effluent from the anaerobic bioreactor through a strictly anaerobic bioreactor comprising an immobilized methanogenic microbial consortia which metabolize the VFA's and produce methane.

In another aspect of the invention, the invention comprises a process of treating wastewater containing biodegradable suspended solids and/or organic compounds, said process comprising the steps of:

(a) passing the wastewater through a facultative anaerobic bioreactor comprising a microbial consortia which produces hydrolyzing enzymes which breakdown the solids and/or organic compounds in the wastewater and which produce volatile fatty acids as a result of facultative anaerobic processes; and (b) passing at least a portion of the effluent from the facultative anaerobic bioreactor through a strictly anaerobic bioreactor comprising a methanogenic microbial consortia.

In one embodiment, the process does not include any step of settling and removing solids from the wastewater prior to step (a). The effluent from the strictly anaerobic bioreactor may be further treated to remove one of or a combination of any of the following: P-containing compounds, N-containing compounds, BOD, COD and /or suspended solids.

In another aspect of the invention, the invention comprises a nitrogen removal bioreactor apparatus comprising:

(a) an anoxic denitrification bioreactor having a liquid inlet, a liquid outlet and a gas outlet and comprising a microbial consortia which reduces nitrogen oxides to nitrogen gas;

(b) an aerobic nitrification bioreactor having an inlet and an outlet and comprising a microbial consortia which oxidizes ammonia to nitrogen oxides;

(c) means for connecting the outlet of the denitrification bioreactor to the inlet of the nitrification bioreactor for transferring liquid from the denitrification bioreactor to the nitrification bioreactor; and (d) means for recycling at least a portion of effluent from the outlet of the nitrification bioreactor to the inlet of the denitrification bioreactor.

In one embodiment, the apparatus may further comprise means for aerating or oxygenating the nitrification bioreactor. The connecting means may comprise a system which transfers liquid from the denitrification bioreactor to the nitrification bioreactor when the liquid reaches a predetermined level within the denitrification bioreactor. The transfer system may proportionally slows down the rate of liquid transfer as the liquid level within the denitrification bioreactor is reduced. The connecting means may preferably be a siphon system which is gravity operated.

In one embodiment, the denitrification bioreactor is a substantially cylindrical container and the nitrification bioreactor is an annular container which surrounds the denitrification bioreactor. Flow within the denitrification bioreactor is preferably non-plug flow.

In yet another aspect of the invention, the invention comprises an integrated unitary bioreactor for removing organic solids, BOD and/or nitrogen compounds from a wastewater stream, comprising:

(a) an anaerobic fermentation chamber comprising immobilized facultative anaerobic microbes and having an inlet and an outlet;

(b) a combined BOD/nitrogen removal chamber comprising a first microbial population of heterotrophic aerobic microbes, a second population of aerobic nitrifying microbes and a third population of anoxic dentrifying microbes and having an inlet connected to the anaerobic chamber outlet and an outlet;

wherein the mixture of the first, second and third populations of microbes adjusts in response to the relative level of BOD, nitrates and ammonia introduced into the BOD/nitrogen removal chamber.

In one embodiment, the bioreactor further comprises an gas dissolving system for introducing oxygen into the BOD/nitrogen removal chamber such that an upper portion of said chamber is aerobic. The gas dissolving system may also introduce ozone into the BOD/nitrogen removal chamber.

In one embodiment, the first and second populations of microbes dominate an upper portion of the BOD/nitrogen removal chamber and the third population dominates a lower portion of said chamber. The effluent from the anaerobic chamber may be introduced into the lower portion of the BOD/nitrogen removal chamber.

In one embodiment, the bioreactor further comprises a siphon system which draws liquid from the BOD/nitrogen removal chamber to an effluent chamber and a liquid recycling system which draws liquid from the effluent chamber and distributes it at the top of the BOD/nitrogen chamber. The liquid level in the effluent chamber may be controlled by a level controller and a pump which pumps liquid to a discharge or back to the BOD/nitrogen chamber.

BRIEF DESCRIPTION OF THE DRAWINGS

For a further and clear understanding of the present invention, exemplary embodiments of the present invention will now be described in conjunction with the accompanying drawings in which like components and process units are given like reference numerals, and wherein:

FIG. 5 shows a schematic representation of a retrofit of an embodiment of the invention into an existing prior art biotreatment system.

FIG. 6A shows a schematic representation of an embodiment of the invention which implements a simple process for simultaneous removal of TSS and BOD, and partial removal of TN. FIG. 6B shows a unitary integrated bioreactor in vertical cross-section which may implement the process depicted in FIG. 6A.

FIG. 9 shows the preferred biokinetics for P-removal at three different initial P concentrations over a period of 140 minutes.

FIG. 10 shows the effect of BOD (substrate or representing VFA concentration) to total P (TP) ratio on the P-removal over a period of 140 minutes.

FIG. 11 compares the biodegradable solid distribution before and after anaerobic immobilized living cell bioreactor treatment (in brewery wastewater).

FIG. 12 shows the COD reduction through the treatment of various immobilized bioreactors during steady state operation.

FIG. 13 shows the removal of TSS through various immobilized bioreactor system under steady state operation.

FIG. 14 shows the reduction of $NH_3$-N through various immobilized bioreactors under steady state operation.

DETAILED DESCRIPTION OF THE INVENTION

Figure 1:
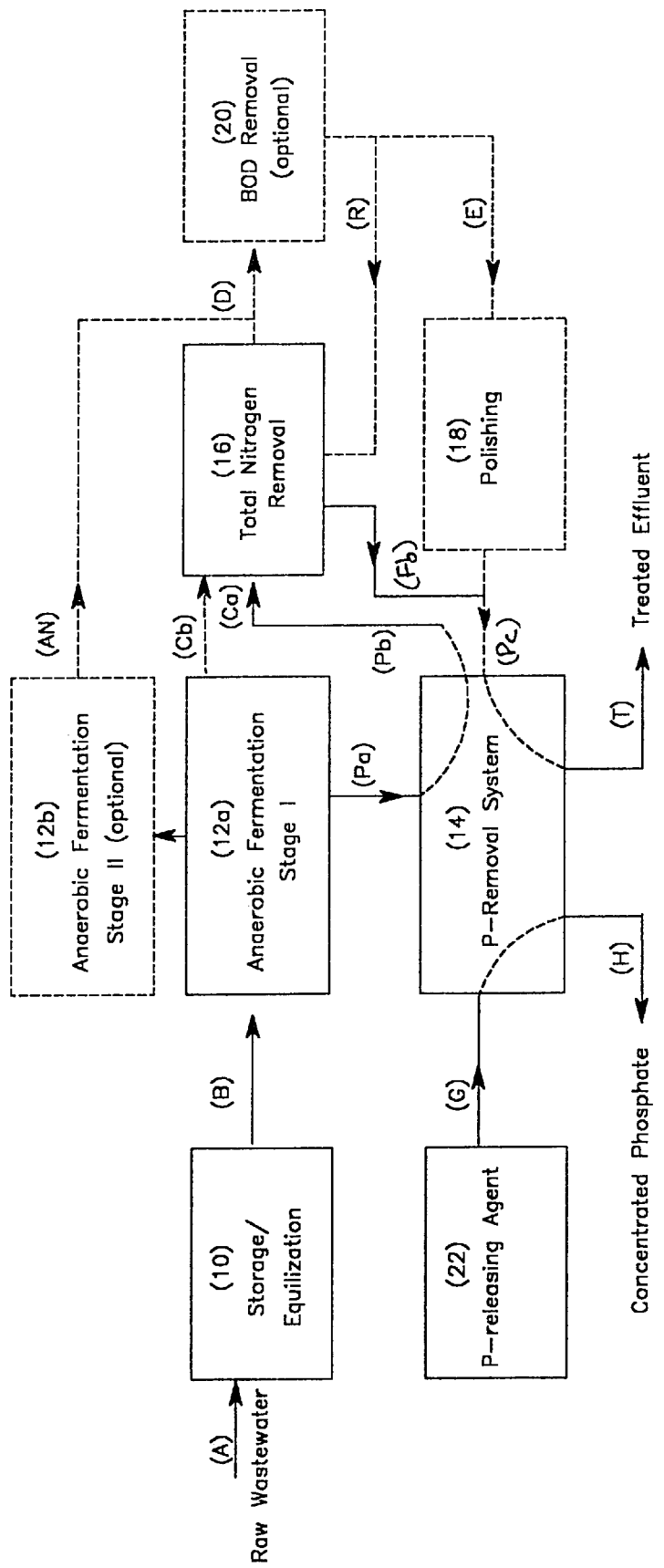
FIG. 1 shows a schematic depiction of the integrated biological processes and the immobilized living cell bioreactor system of the present invention.

The present invention provides for new methods and apparatuses for biological nutrient removal from wastewater using selected or acclimatized microbial consortia immobilized within biomedia in integrated bioreactor systems.

DEFINITIONS

The term "anaerobic process" refers to a biological process that occurs under the conditions where there is no dissolved oxygen is present in the bulk liquid. A "facultative process" refers to a biological process in which the microorganisms involved can function properly in the presence or absence of molecular oxygen. A "strict anaerobic process" refers to a biological process in which the microorganisms involved can only function properly in the absence of molecular oxygen.

The term "anoxic process" is defined as a biological process that occur in the absence of free dissolved oxygen or very low dissolved oxygen conditions. This process is usually used by the denitrification bacteria that convert the $NO_3$-N into the nitrogen gas.

The term "nitrogen" or "N" refers to organic or inorganic nitrogen containing compounds dissolved or suspended in aqueous phase that are to be broken down and removed in subsequent biological processes. In a nitrification process, "nitrogen" may mean $NH_3$-N, and in denitrification process, "nitrogen" may mean $NO_{3\text{-}N \text{ or } NO_2}$-N and related forms.

The term "phosphorus" or "P" refers to organic or inorganic phosphorus containing compounds dissolved or suspended in aqueous phase that are to be broken down to ortho-P ($PO_4$-P) and subsequently removed from the wastewater. In P-removal process, Pi means $PO_4$-P.

The term "biological nutrient removal" is the term applied to the removal of soluble and insoluble but biodegradable BOD, nitrogen and phosphorus.

The term "bioreactor" refers to an enclosed or partially enclosed chamber comprising biosupports or biomedia with living microorganisms or microbial consortia immobilized under growth conditions.

The term "volatile fatty acids" or "VFAs" refers to short-chain organic acids which may be favourable metabolic substrates for microbes and $PO_4$ and denitrification microbes in particular.

DESCRIPTION

The integrated biotreatment processes of the present invention comprises anaerobic, anoxic, general aerobic and/or obligate aerobic biological processes, arranged so that the effluent or the products in the effluent (either solid, liquid, or gas) from one biological process may be used by another biological process in the system. Preferably, the processes are so designed that one biological process may be a pretreatment process for another that effectively prepares the necessary conditions and contents that allow the another biological process to have enhanced efficiency and reliability.

The processes in this invention are designed to minimize cross contamination between different bioreactors and to preferably enhance the efficiency of each type of bioreactor. In a preferred embodiment, different types of bioreactors work somewhat independently of each other to treat the effluent in different stages. The oxidation and reduction potential (ORP) may be integrated with the hydraulic retention time and substrate conditions to ensure the selective immobilization and the stability of the desired microbial consortia in each bioreactor. By passing the raw wastewater from an initial anaerobic bioreactor to the next desired one, in a series of steps outlined in this invention, wastewater may be cleaned in a highly efficient manner.

Referring to FIG. 1, an embodiment of the inventive method may be summarily described as follows. The three main components of this embodiment include an anaerobic bioreactor (12), a P-removal bioreactor (14) and a nitrogen removal bioreactor (16).

The choice of appropriate initial seed microbial consortia for each of the within described bioreactors are well within the skill of one skilled in the art of microbiological biotreatment and environmental engineering. Many appropriate or suitable microbial consortia are available from recognized depositories of biological material.

In the first step of one embodiment of this process, screened wastewater (A) may be fed directly into the bottom of the anaerobic bioreactor (12), however, in an alternative embodiment, an equalization and storage tank (10) may be placed upstream of the Stage I anaerobic bioreactor (12a).

In the Stage I anaerobic bioreactor (12a), immobilized facultative microbial consortia hydrolyze the complex or suspended organics and ferment them into volatile fatty acids (VFAs). As well, complex N compounds are broken down primarily into ammonia and complex P-compounds are broken down into orthophosphate. The VFA's may then be used by other microbial consortia in downstream bioreactors for P-removal and denitrification. As a result, it may be unnecessary to add a carbon source to the system. Usually in a conventional system, it is necessary to add excess methanol or other carbon sources in order to obtain efficient denitrification and P-removal.

In the anaerobic bioreactor (12a), biodegradable organics in soluble and suspended solids forms are fermented into VFAs as indicated above. FIG. 11 demonstrates the effect of anaerobic treatment on the size of suspended solids that are biodegradable. It shows that after anaerobic treatment, almost 90% of large size suspended solid particles are fermented into the forms that are smaller than 50 mesh or converted to VFAs. More than 70% of organics are in size of 100 mesh or smaller, most of them are fermented into VFAs. As a result, the effluent from the anaerobic bioreactor (12a) will have low TSS content and high level of VFAs, $NH_3$ and $PO_4$.

The pH in the bioreactor (12a) is preferably maintained between 5 to 6.5 and the ORP is between −250 mV to 0 mV, preferably greater than −200 mV. These conditions help ensure that the anaerobic bioreactor (12a) can selectively immobilize and maintain the initial seed microbial consortia and keeps them in dominant and competitive status.

The effluent stream (Pa) from the anaerobic bioreactor (12a) then flows into a P-removal bioreactor (14), where immobilized P-removal microbes uptake and store the VFAs from the effluent (Pa) in the microbial cells, in what is herein referred to as a P-recharge process. After P-recharge, the wastewater stream (Pb to Ca) containing residual VFAs and other nutrients from P-recharge process is directed into a nitrogen removal bioreactor (16) comprising an anoxic denitrification bioreactor (16a) and an aerobic nitrification bioreactor (16b).

If P-removal is either unnecessary or undesired, the effluent from the anaerobic bioreactor (12a) may be directed directly to the N-removal bioreactor (16) by stream (Cb).

In the denitrification bioreactor (16a), the anoxic microbial consortia convert $NO_2$ and $NO_3$ into $N_2$ gas using residual VFAs as their carbon and energy sources. The effluent is then passed to the aerobic nitrification bioreactor (16b) where $NH_4$-N is oxidized to $NO_3$. As well, residual organic solids or BOD may be polished out by the microbial consortia at this stage. A portion of the effluent from the nitrification bioreactor (16b) may be recycled back to the denitrification bioreactor (16a) to reduce the $NO_3$ level in the effluent.

The effluent from the nitrogen removal bioreactor (Fb to Pc) may then be passed to a P-removal bioreactor (14A, B, or C) containing the microbial consortia which has been recharged. The microbes in the P-removal bioreactor may then uptake and store $PO_4$-P using the previous stored VFAs as carbon and energy sources and under vigorous aerobic conditions. After P-removal, the stream (T) can be directly disposed of or re-used.

Nitrogen Removal Bioreactor

Effluent stream (Ca) is delivered to the bottom of the anoxic denitrification bioreactor (16a) through a distribution system (17). The ORP in the denitrification bioreactor (16a) is controlled between about −250 to about 50 mV, preferably around −100 to 0 mV, which helps to maximize the efficiency of the denitrification process and keep the appropriate microbial consortia competitive and dominant. Residual VFAs from the P-recharge stream further enhance the efficiency and kinetics of denitrification biological process.

Once the fluid level in the denitrification bioreactor (16a) reaches a predetermined level, a siphon system (20) automatically draws denitrified effluent from the denitrification chamber (16a) and uniformly distributes it onto the top of aerobic nitrification bioreactor (16b). When treating normal domestic sewage, the top portion of the nitrification bioreactor (16b) usually functionally serves as a BOD and TSS polishing bioreactor. The top portion is usually dominated by heterotrophic bacteria, which can effectively reduce the BOD and TSS in the wastewater before it reaches the lower portion. The lower portion of this bioreactor is dominated with nitrification bacteria in a DO rich environment. In one embodiment, the fluid level is controlled at about 40% of the height of the nitrification bioreactor. Therefore, the top portion of the nitrification bioreactor (18) is not submersed in the liquid as the anaerobic (12) and anoxic (16a) bioreactors are. Gaseous oxygen is therefore available to the wet biomass directly. As the waste stream moves down through the biomedia by gravity, the residual organic and TSS concentration may be reduced to so low a level that it makes the heterotrophic bacteria less competitive relative to the nitrification bacteria. Thus, in the nitrification bioreactor (16b) the wastewater flows from top, the BOD zone, gradually down to the bottom, where the wastewater will have very low BOD, and autotrophic nitrification bacteria will predominate and nitrification efficiency will be maximized.

The siphon system (20) reduces energy consumption and may make the system more reliable biologically and mechanically because it reduces the need for moving parts such as pumps and valves. Preferably, the siphoning rate is higher at the beginning stages when the bacteria are in a hungry status, and the siphoning rate is gradually reduced along the rates of the removal as the bacteria are gradually saturated. A gap between siphon cycles allows the bacteria to further remove the left over substrates before the siphon (20) refills the nitrification bioreactor (16b) from the denitrification bioreactor (16a).

Figure 2:
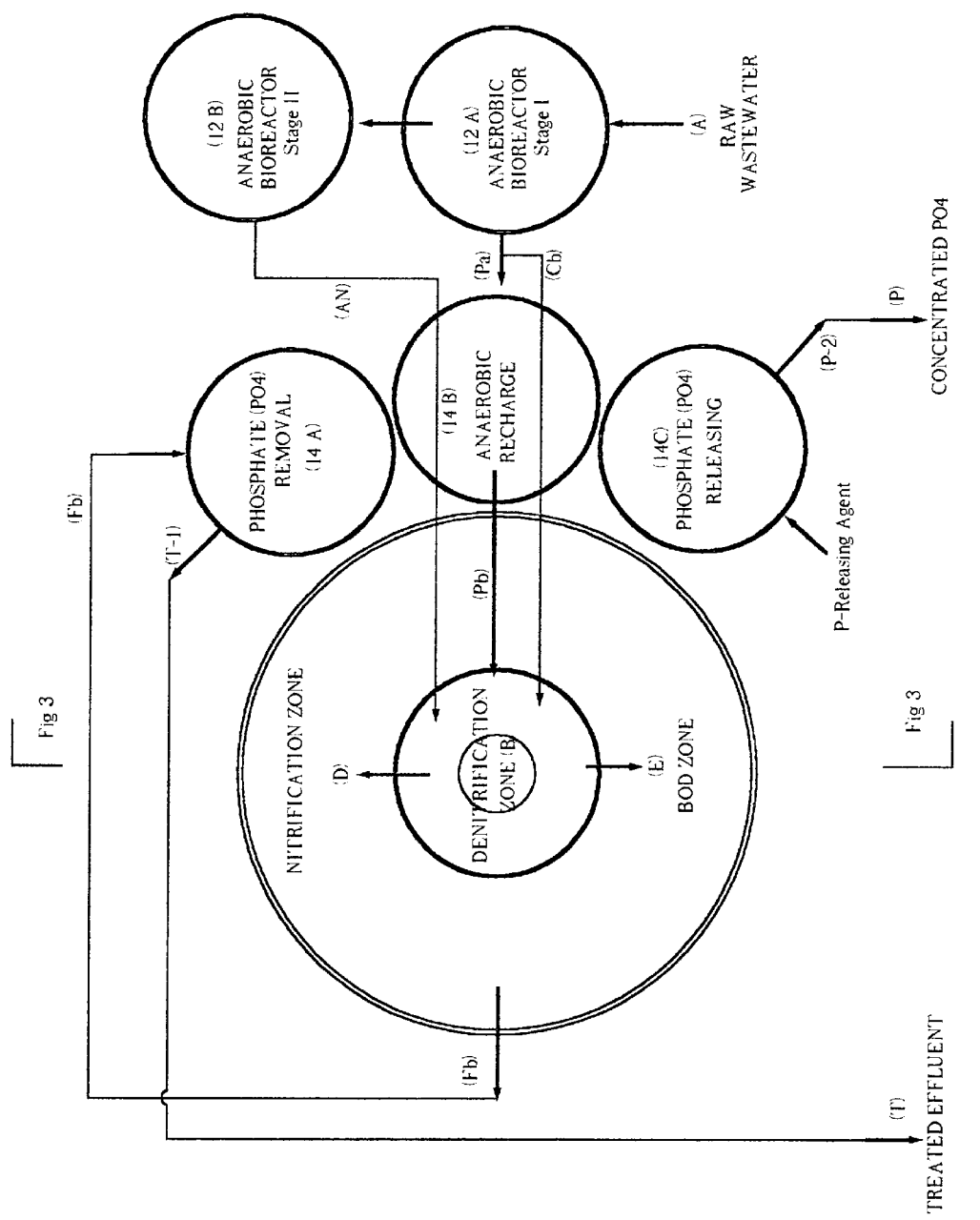
FIG. 2 is a plan view of an integrated BOD/nitrification/denitrification/P-removal bioreactor configuration of the present invention.
Figure 3:
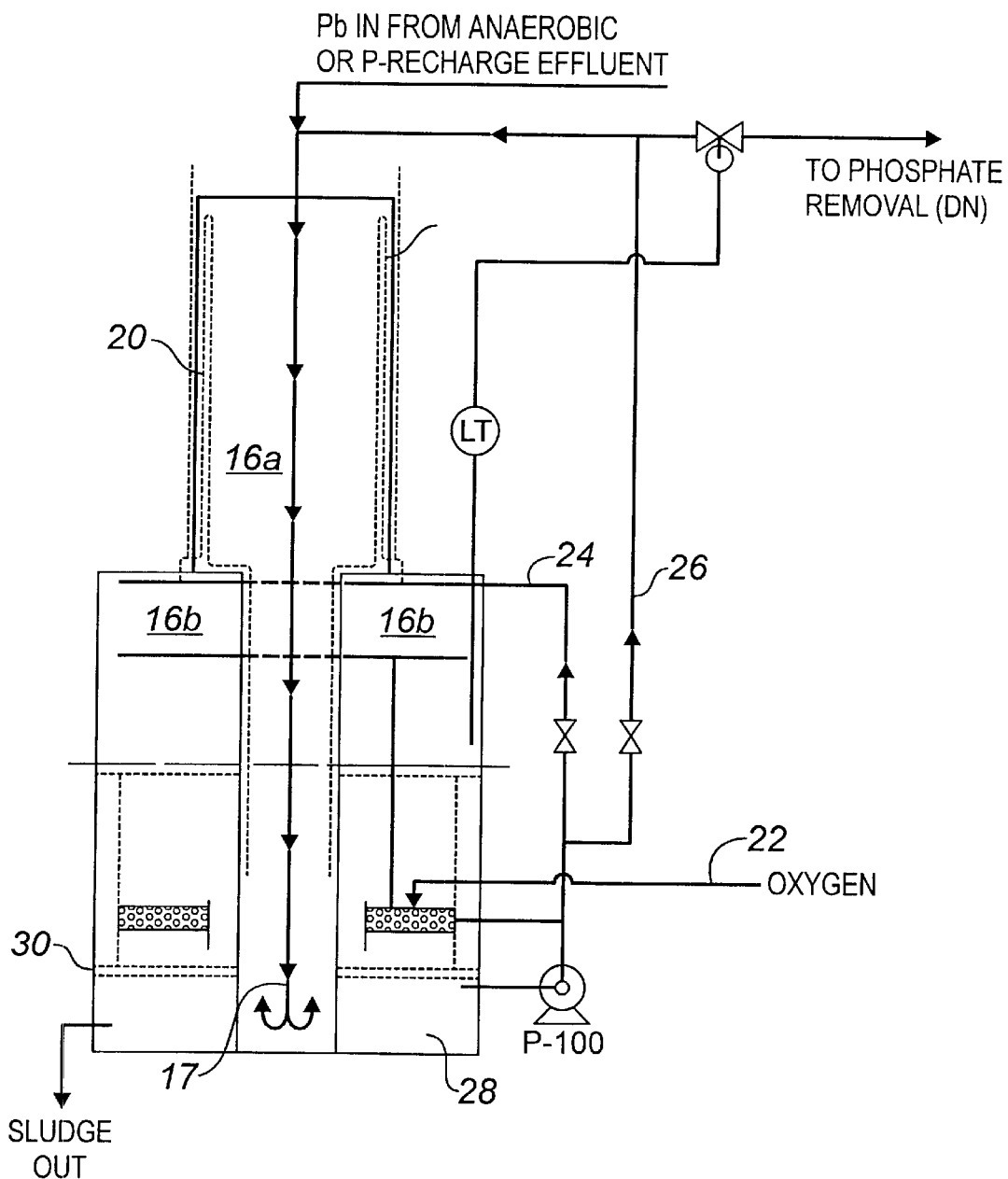
FIG. 3 is a vertical cross-sectional view of the integrated BOD/nitrification/denitrification bioreactor system shown in FIG. 2.

In the embodiment illustrated in FIGS. 2 and 3, the denitrification and nitrification bioreactors are separate bioreactors. As may be appreciated by one skilled in the art and as described with reference to FIG. 6 below, the function of the two bioreactors may be accomplished by one bioreactor having different zones with different dominant microbial consortia.

The dissolved oxygen level in nitrification bioreactor (16a) is preferably maintained between 1.25 to 3 mg/L, more preferably at about 1.75 mg/L by use of a conventional oxygenation system (22). The atmosphere at the top of the nitrification bioreactor is therefore oxygen enriched. Thus, the nitrification bacteria can efficiently convert $NH_3$ to $NO_3$. If the initial concentration of total N and organics in the raw wastewater is high, a portion of wastewater from nitrification chamber may be recycled (24) back to the top of the nitrification bioreactor (16b). The recycle ratio can vary from 0.25 to 2.5 of inlet flow rate, depending upon the initial ratio of organic/TN. A portion of recycled stream may be diverted (26) into the top of denitrification bioreactor (16a) for continuous conversion of $NO_3$ to $N_2$, resulting in the desired removal of nitrogen from the wastewater.

At the bottom of the nitrification chamber is a sludge compartment (28) which is separated from the biomedia containing portion of chamber by a screen (30). Although sludge production should be minimal, a small amount of sludge will accumulate in this chamber (28) and must be periodically cleared out. This sludge may be directed to anaerobic Stage I bioreactor (12a) for processing rather than being wasted.

P Removal Bioreactor

The effluent (Pc) from the nitrification bioreactor may be transferred directly into one of the P-removal chambers (14) in which the bacteria have already been recharged with the effluent (Pa) from the anaerobic bioreactor containing VFAs. The DO level in P-removal bioreactor (14) is preferably kept between about 3 to about 5.5 mg/L, and more preferably between about 3 to about 4 mg/L, by using of an oxygenation system, and a gas with a high oxygen content, preferably >90% oxygen content. In this bioreactor (14), the P in the wastewater will be removed and some organic residuals will also be further polished out. The effluent (T) from this reactor may have a very low concentration of organics, TSS, TN and TP and thus can be disposed of. A disinfecting step may be added on if desired or necessary.

The P-removal process may be designed that the VFA enriched effluent (Pa) is supplied to the P-removal bacteria under favourable conditions. Furthermore, the bioreactor and loading time are so designed that the fully recharged bacteria are allowed to uptake the P up to 75 to 85% of its capacity before transition to a P releasing stage, which should be sufficient to remove sufficient P to meet reasonable discharge criteria. More importantly, the absorbed P is then directly recovered from the immobilized biomass instead of wasting the P containing biomass that usually occurs in the prior art.

Figure 4:
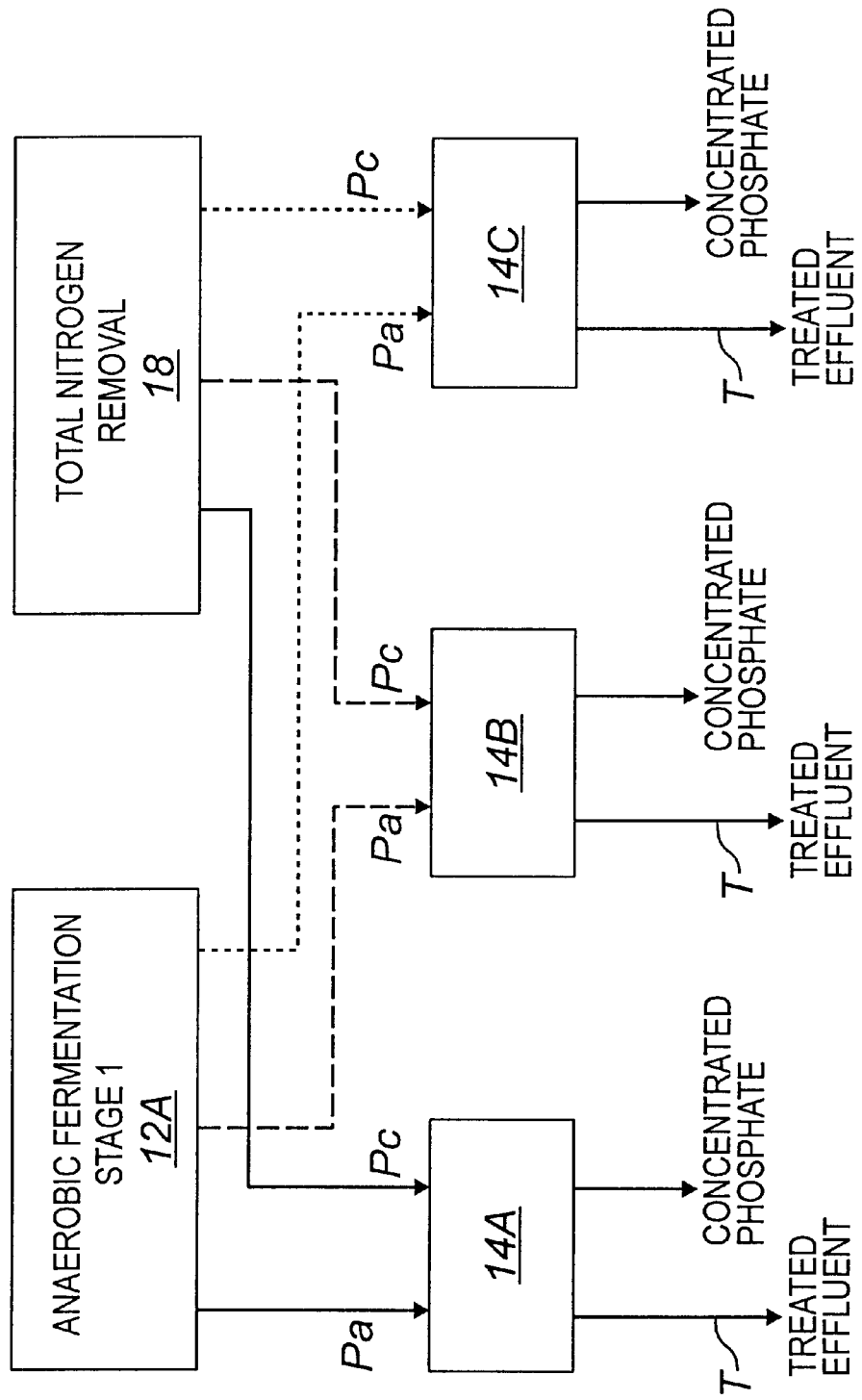
FIG. 4 shows the configuration and operational sequence of a preferred P-removal bioreactor system described in present invention.

In a preferred embodiment schematically represented in FIGS. 2 and 4, there are three identical P-removal bioreactors (14A, 14B, 14C) allowing for continuous P-removal. These three bioreactors work in sequential batch mode that consists of three working periods or phases: anaerobic or VFA recharge, P-removal and P-release. Specifically, in the example shown, the bacteria in chamber A go through the P release phase while the bacteria in Chamber B are in P-removal phase and the bacteria in P-removal chamber C are in recharge phase.

The VFA recharge is the first period that allows the bacteria to contact with VFA rich stream and rapidly uptake and store sufficient VFAs in the microbial cell under anaerobic conditions. These stored VFAs will be used as a carbon and energy source in the following aerobic P-removal period.

As an example, for normal domestic sewage treatment application, in the preferred embodiment, each Pi removal chamber is operated in following sequential mode:

a) P-recharge, Ta=37.5 minutes;
b) P-removal, Tb=50 minutes;
c) P-release and washing, Tc=25 minutes;
d) Back to P recharge.

In this mode and in an embodiment, the Tb and Tc can be selected with wastewater characteristics and treatment system, then the Ta can be easily determined with Ta=(Tb+Tc)/2. However, in a preferred embodiment, the Ta should be longer than the minimum recharge time, which may be determined by one skilled in the art. If the Ta calculated is smaller than the minimum, the Tb and Tc may be adjusted to meet the minimum.

After the P-removal phase, the P-bioreactor with high intracellular P levels is ready for the P-release cycle. A P-release agent is introduced into the bioreactor and the contacted with the bacteria for the effective period of time, usually not less than 20 minutes, under anoxic or anaerobic conditions. Using this preferred method, more than 90% of the absorbed P is released into the solution, creating a concentrated $PO_4$ solution. This concentrated P solution may then be sent to a recovery process that recovers the $PO_4$ as a fertilizer or a useful chemical. After recovery, the P-releasing agent is recycled back to process for reuse. The fresh P-releasing agent is added to make up the volume lost.

Preferably, a certain amount of fresh P-releasing agent is used to rinse the biomedia before it is recharged for the next cycle.

The P-releasing agent may be any well-known solution which promotes the release of P from bacterial cells and is preferably a solution of Tween 20 and the effluent from the anaerobic bioreactor. As a stock solution, the concentrated P-releasing solution may be made of:

Non-dilute effluent (Pa) from the anaerobic bioreactor I 0.01% (w:v) of Tween 20 pH=5.5 to 5.7 (adjusted with HCl acid).

In a preferred embodiment, the reconstituted P-releasing solution (recycled mixed with fresh solution) may contain about 5% v/v of raw anaerobic effluent and about 5 mg/L Tween 20.

It will be obvious to those skilled in the art that the duration of each P-removal process and the P-releasing agent used are modifiable and may be modified according to the characteristics of raw wastewater and the desired removal of P in the final effluent.

The time (Ta) for this period varies with the concentration of VFAs, total phosphorus, temperature and other growth conditions. For TP <15 mg/L and with BOD/TP>15, the Ta usually last for 25 to 30 minutes. The second period is P-removal stage. The wastewater stream (Fb) containing $PO_4$-P is brought to contact with the recharged bacteria in the first period. The recharged bacteria can uptake the P from the wastewater in excess amount and store them in the cells in polyphosphate forms. Thus, after the contact, the P in the wastewater is removed from the wastewater. The biokinetics of the P uptake is dependent on many factors such as the initial P concentration, the VFA/TP ratio, the food/microorganism ratio ("F/M or VFA/M"), solids retention time ("SRT"), temperature and other factors. In a treatment system, SRT and biomass concentration are usually set at a relative constant. Thus, the major factors are initial concentration and VFA/TP ratio that may have significant effect on the performance of a treatment system.

FIG. 9 shows the effect of initial concentration and contact time on the residual P concentration in the wastewater. The data represented in FIG. 9 suggests that the P uptake kinetic pattern is similar to each other among different initial P concentration but the biokinetics increases with the increase of the initial P concentration in the wastewater. In addition, it shows that the kinetics keeps almost constant within first 30 minutes contact. Then, it slows down into transition periods that last from 30 to about 60 minutes. After 60 minutes, the kinetics becomes slower, probably because of the microbial cells getting close to its saturation limits or because of depletion of substrates or nutrients. Thus, in one embodiment of this invention, the contact time may be designed to be 30 to 70 minutes for optimum P-removal efficiency depending on the wastewater and the desired level of Pi removal.

FIG. 10 illustrates the impact of VFA/TP ratios on the Pi removal and the residual Pi concentration. The results in FIG. 10 demonstrated that when BOD/TP ratio is less than 15, the Pi uptake kinetics increases significantly with the increase of BOD/TP ratio. However, when BOD/TP ratio becomes greater than 15, the increase is insignificant. Thus, a preferred range will be about 10 to about 20. If the wastewater has low BOD and high P, the BOD/TP can be set as low as about 12 and that will have little impact on the Pi removal. This is mainly because the effect of immobilization that provides high bacterial cell density and relatively low equivalent SRT (solids retention time).

FIGS. 12, 13 and 14 shows the reduction of COD, TSS and Nitrogen content from brewery wastewater. It demonstrated that each bioreactor system could effectively remove the desired pollutants as designed. The performance is stable and reliable.

A schematic view of an embodiment of a bioreactor configuration is depicted in FIGS. 2 and 3. FIG. 2 shows the preferred embodiment of the P removal system, where bioreactor 14a is in P removal phase, bioreactor 14b is in anaerobic or VFA recharge phase while bioreactor 14c is in P release phase. Also shown in FIG. 2 is the configuration of the nitrogen removal bioreactor (16) having a denitrification zone and a BOD removal/nitrification zone as described above. The cross-sectional view in FIG. 3 shows the siphon system (20) which transfers effluent from the denitrification zone (16a) to the BOD/nitrification zone (16b).

If the wastewater to be treated (A) has a high concentration of organics, any one or more of the following types of bioreactors may be added to the system.

Firstly, a Stage II anaerobic bioreactor (12b) may be provided to recover energy in the form of methane gas. In this strictly anaerobic bioreactor (12b), methanogenic microbial consortia then convert the previous VFA's from the Stage I bioreactor(12a) to methane. The Stage II bioreactor (12b) has little impact on $NH_3$ and $PO_4$ in the wastewater. The effluent from the Stage II bioreactor (12b) may be passed directly to a BOD bioreactor (20) as described below.

Secondly, a separate aerobic BOD bioreactor (20) may be provided to reduce the BOD loading to the nitrogen removal bioreactor (16). If a Stage II anaerobic bioreactor is provided, the effluent stream (AN) from Stage II anaerobic bioreactor is first mixed with the denitrified stream (D) and together flows into BOD bioreactor (20). It is preferred not to direct this stream (AN) into the N-removal bioreactor (16) before BOD removal in bioreactor (20) if there is a high level of residual organic material. If N removal is desired, the effluent from bioreactor (20) may be recycled back to N removal bioreactor (16) as shown by stream (R).

Thirdly, an aerobic polishing bioreactor (18) may be provided to oxidize some of the residual $NH_4$-N out of the wastewater and to further reduce residual organic solids to meet the desired level of removal.

Periodically, all the bioreactors will need to be cleaned to regenerate the portion of the biomedia surface and internal microchannels that may be occupied by dead cells or inorganic deposits or non-biodegradable matters. The frequency of cleaning of the bioreactors are in the relative order of: anaerobic (12)>P-removal (14)>denitrification (16a) >nitrification (16b)>polishing (20). The nitrification bioreactor (16b) may only require one cleaning every 3 to 5 years, depending upon the composition of the wastewater.

EXAMPLES OF RETROFIT APPLICATION

In another aspect of the invention, the system may be designed that it allows dealing with different characteristics of wastewater and may be designed as a new treatment system or be retrofitted into existing biotreatment facilities. FIG. 5 shows that any of three typical existing system can be effectively converted into a biological nutrient removal system using the bioreactor system described in this invention. More precisely, each bioreactor system can be easily retrofit into one of the three typical existing biotreatment systems for N removal, P-removal or simultaneous N and P-removal. A nitrogen removal bioreactor (16) system described in FIGS. 2 and 3 can be added to the system after the secondary clarifier. Based on the treatment requirement, a polishing bioreactor system (20) may be used to ensure the effluent meet discharge criteria. For the wastewater with low N and high P, the nitrogen removal bioreactor may be removed from the process. Similarly, the P-removal bioreactor system can be optional or added on to an existing system depending on the wastewater and regulation requirements. These options and alternatives further demonstrates that skilled people in this field may easily modify this invention for other purposes.

As shown in FIG. 5, for example, in an activated sludge process, the aeration tank may be converted into an immobilized bioreactor using biomedia. In this application, the primary clarifier may be converted into the immobilized anaerobic bioreactor (12a) that liquefies the biodegradable solids and complex organic compounds into VFAs or easily biodegradable organics for the following biological processes. The secondary clarifier may be converted into denitrification or nitrogen removal bioreactor depended on the wastewater and size and design of existing clarifier. If the existing secondary clarifier is not large enough for this purpose, a polishing bioreactor may be added for this application.

FIG. 6 illustrates another application of this invention for a simple integrated single tank biotreatment system. The biotreatment system described and shown in FIGS. 6A and 6B is a single tank (100) having an interior that is compartmentalized into four chambers. The first chamber (102) serves as wastewater receiving and equalization chamber, in which large debris or non-biodegradable matter are retained. The wastewater flows by gravity into the second anaerobic biotreatment chamber (104). In the second chamber, the organic TSS or complex organic materials are first converted into low molecular organics such as VFAs, and subsequently degraded to a degree of about 50 to about 70% by the facultative microbial consortia immobilized on the biomedia (not shown). The accumulated gas from the aerobic chamber (106) periodically mixes at the top of anaerobic bioreactor (104) where the residual oxygen in the gas may keep the bioreactor (104) under facultative conditions.

The anaerobic treated wastewater is introduced into the anoxic zone of aerobic chamber (106) along a channel between the dividing wall (108) and biomedia. Organic compounds are first used for removal of $NO_3$.in the anoxic zone (106a) if desired. After denitrification, the residual organics in the liquid then comes into contact with the biomass immobilized at the top portion (106c) of the biomedia. This portion of biomedia is exposed to the air during the siphon cycles, thus oxygen is readily available to the microorganisms immobilized in the biomedia. In addition, in one embodiment, a venturi and gas dissolving system (108) may add D.O. and/or ozone into the liquid that is pumped to the top. By adjusting the organic loading, recycling rate and level of DO in the liquid, the second chamber from top to bottom can be divided into BOD (106c), nitrification (106b) and denitrification (106a) zones. The height of each zone depends on the organic loading, concentration of N as well as the rate of recycling and DO addition. The system only requires a pump and two level controllers for continuous operation. In one embodiment, the operation of the pump (110) and oxygenation system (108) is so designed that it can dissolve ozone and oxygen at same time while it brings the liquid to the top of bioreactor (106) for uniform distribution or to the discharge outlet (112).

In one embodiment, the effluent from the aerobic chamber (106) may be further polished at the upper section of TE chamber (114) and, if desired, disinfected through contacting with ozone from the gas dissolving system (108), then directly discharged in a process that is controlled by the water level in the TE chamber (108).

A siphon system (116) draws effluent from the BOD/N/DN chamber (106) into the TE chamber (114 when the fluid reaches a certain level in the BOD/N/DN chamber (106). The siphon frequency is controlled by hydraulic loading rate and recycling rate. In turn, the siphon and recycling rate controls the liquid level in the BOD/N/DN chamber and the mixing in AN chamber.

The process and bioreactor configuration described in FIG. 6 is most suitable for small on-site wastewater treatment system or so called packaged system. Also, it can be retrofitted into the existing septic tank system or other typical packaged systems.

Biomedia

Suitable biomedia are well-known in the art. Preferred examples of suitable biomedia may comprise a porous polymer, hydraulic channels and microbial support structures. The polymer provides numerous micropores with diameters ranging from 200 to 800 microns in diameter. The micropores can effectively immobilize various microbial consortia and provide them with an environment for them to live and may be designed to minimize sludge production in a biological system. The micropores are linked together through internal microchannels, and the microchannels are connected to the hydraulic channels. The microchannels and hydraulic channels together provide effective transport of substrates including D.O. to the immobilized microbial cells and to allow removal waste metabolites from the microbial cells. As a result, this environment may allow the desired microbial consortia to live longer, 'work' more efficiently and produce less waste biomass (usually called sludge). Preferably, this environment protects them from adverse effects and from being washed out from the bioreactor.

Figure 7A:
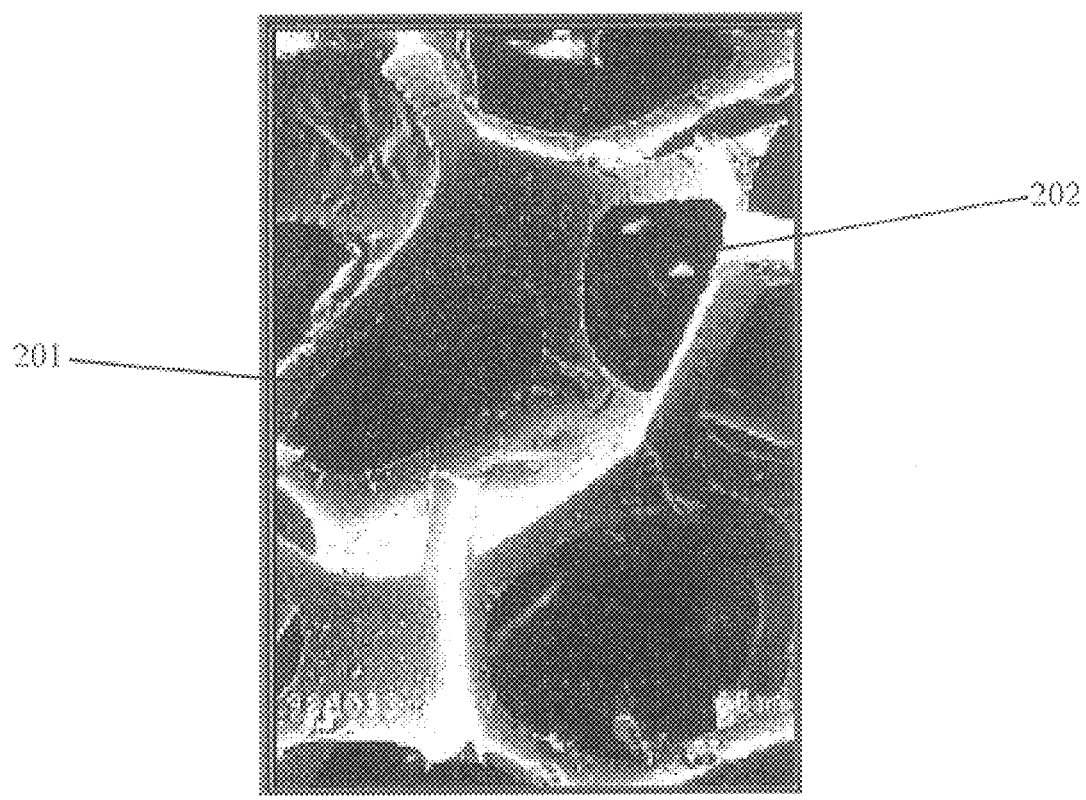
FIG. 7A is a scanning electron microscopy (SEM) image of a cross-section of a biomedia at 50× magnification.

FIG. 7A shows a preferred micropore (201) structure for immobilization of microbial consortia. It also shows the internal microchannels (202) connecting the micropores (201) for the transport of substrates including D.O.

Figure 7B:
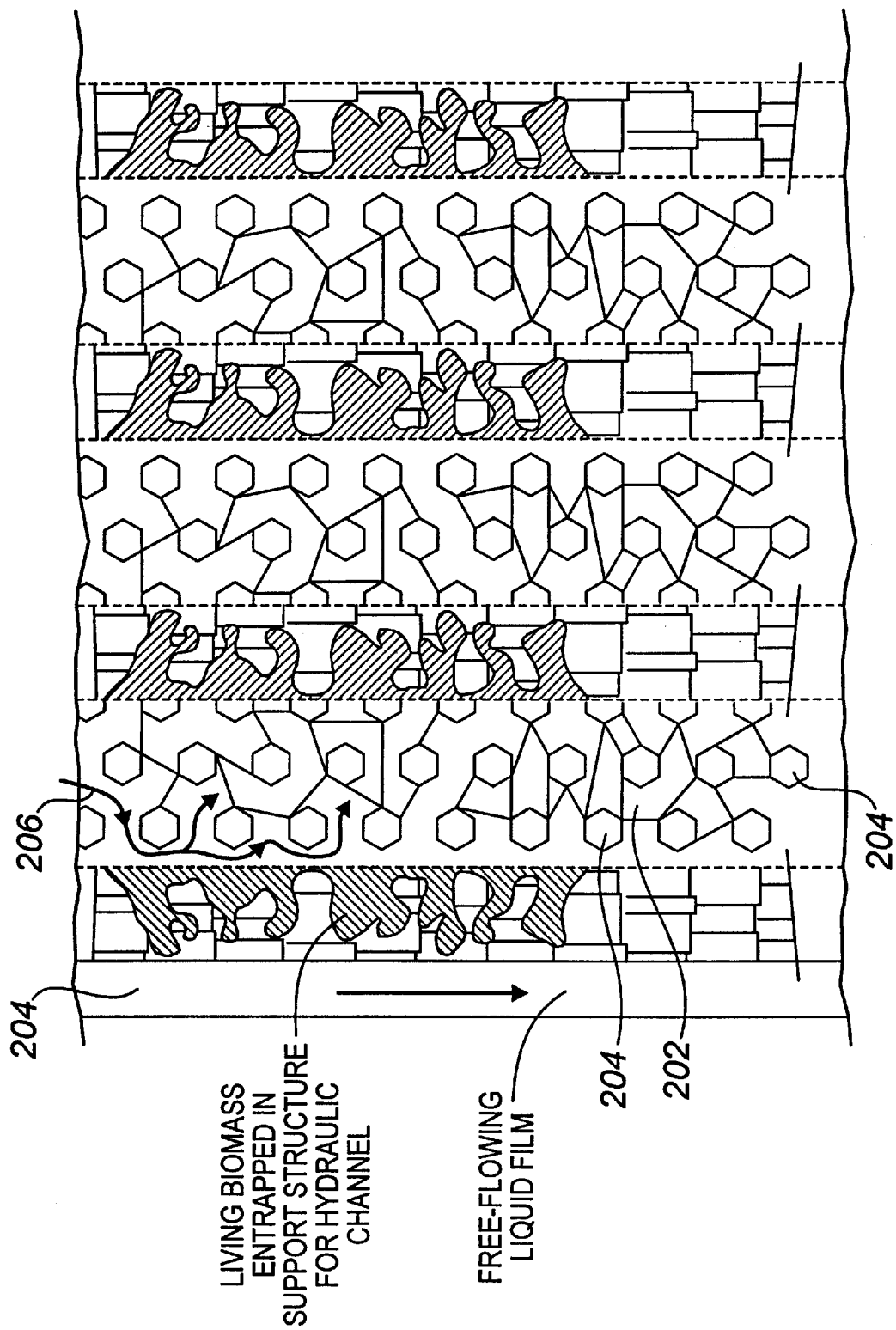
FIG. 7B is a schematic representation of a cross-section of an embodiment of a preferred biomedia showing the hydraulic channels, microchannels and micropores.

FIG. 7b schematically illustrates the support structure for hydraulic channels (204) and the connection of hydraulic channels (204) with the microchannels (202) as well as the liquid diffusion paths (206) within the biomedia (200).

Figure 8:
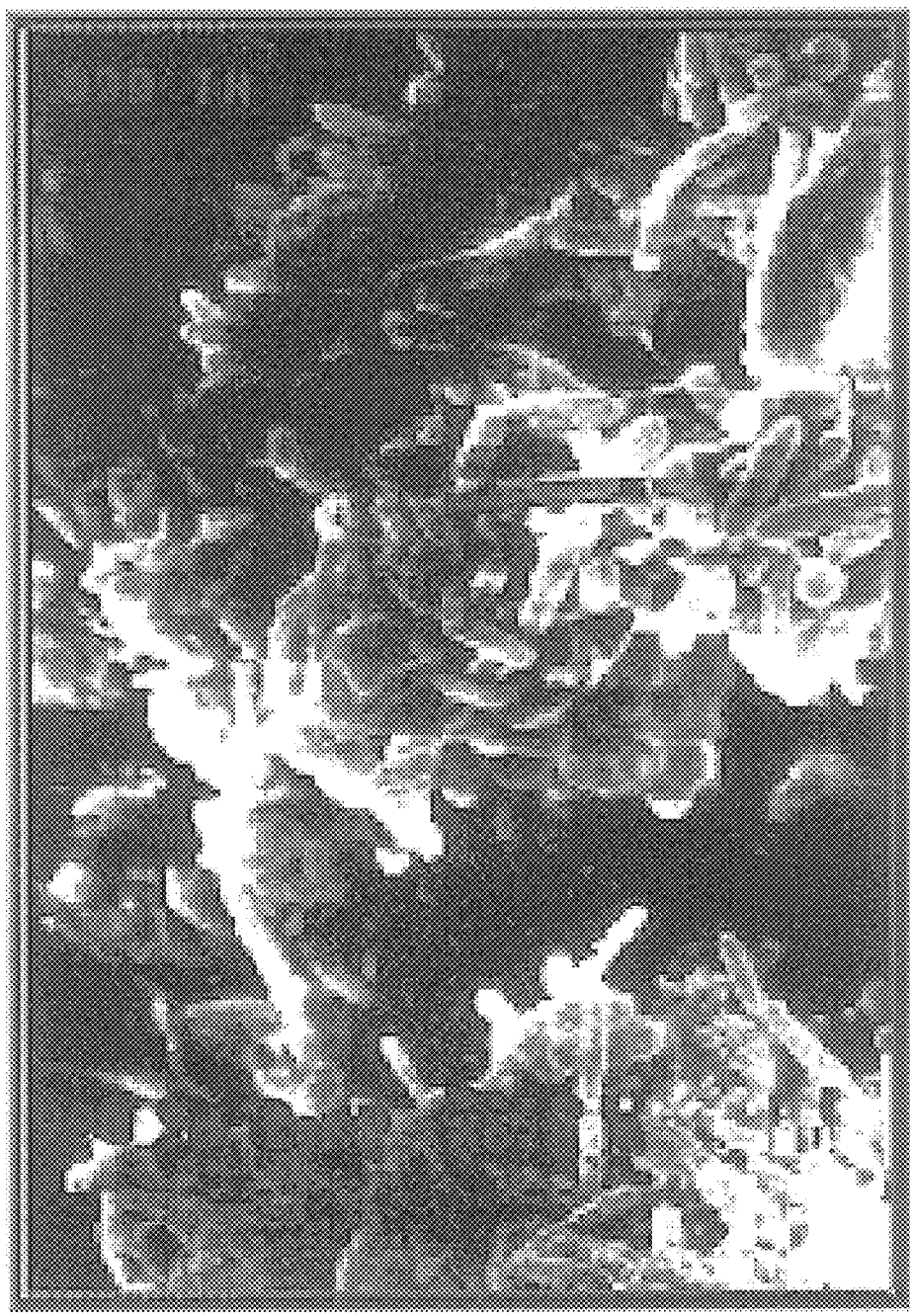
FIG. 8 is a SEM image of microchannels and bacteria immobilized in high density in the above biomedia at 2500× magnification.

FIG. 8 demonstrates the immobilization of bacteria within a micropore (201) that may protect them from shear stress. Within such a micropore (201), the biomass is well protected from being washing out and adverse environmental effects if any. Even if there is an adverse effect that are not prolonged, only the outer layer biomass may be effected and inner biomass may still be protected. Thus after the adverse effect passes, the inner biomass may serve as the seed to rapidly restore the performance of the bioreactor system. This is in sharp contrast to an activated sludge system because the activated sludge system is so designed that all the bacteria in aeration chamber are uniformly distributed and exposed to the environment in order for them have equal opportunity to access to the substrates including DO. These conditions render all bacteria equally exposed to adverse effects when they occur. Also, it is obvious to one skilled in the art that it is vulnerable to be washed out from the bioreactor when the hydraulic loading increases, especially those slowly growing bacteria such as nitrification bacteria.

FIGS. 7 and 8 demonstrate preferred features of biomedia for growth of high density biomass without limitations on mass transfer. The nature and the properties of the biomedia implemented in the embodiments of this invention are not essential to the claimed invention. However, certain configurations of the biomedia will perform better than others. Obviously, ones skilled in the art may make various modifications without departing from the spirit of the technology described in this invention.

Table 1 further lists the angle, the surface to volume ratio and the void volume for each used in the preferred embodiment.

TABLE 1

Specifications for various preferred biomedia

| Type | Angle | Pore Size ($\mu$m) | Surface to Volume Ratio | Void Volume |
|---|---|---|---|---|
| I | 75 to 90 | 500 to 800 | >450 | >90% |
| II | 75 to 90 | 350 to 675 | >600 | >85% |
| III | 75 to 90 | 200 to 450 | >850 | >80% |

The size and distribution of micropores may be optimized for different microbes. For anaerobes, the diameters of micropores may be between 500–800 $\mu$m, with an average size of 620 $\mu$m. For anoxic microbes, the diameters of micropores may be between 350 to 675 $\mu$m, with an average size of 415 $\mu$m. For aerobes and P-removal microorganisms, the diameters of micropores may be between 200 to 450 $\mu$m, with an average size of 275 $\mu$m.

Suitable biomedia may be manufactured in modular blocks. The modular blocks may be configured in two general shapes, circular and rectangular. The dimensions for each shape depend on each treatment system design. For each rectangular block, the zigzag hydraulic transport channels continues throughout the block. The width of the channels may be about 4 to about 6 mm, and the distance between two transport routes may be about 6 to about 60 cm depending upon the block size. For circular blocks, the width of route may also be about 4 to about 6 mm, and the distance between two transport routes may vary from about 5 to about 50 cm depending on the diameter of the block. A 2.5 to 10 cm hole in the middle of the block is preferably provided. In addition, in one embodiment, a 4 cross route may be formed as different location alternately. The transport route in each block may be at about a 75 degree to 90 degree angle approximately with respect to horizontal plan, depending on the type of biomedia. This same angle may also be used in the bioreactor.

As will be apparent to those skilled in the art, various modifications, adaptations and variations of the foregoing specific disclosure can be made without departing from the scope of the present invention.

What is claimed is:

1. A process of treating liquid contaminated with organic compounds, BOD, COD, N containing compounds and/or P containing compounds, said process comprising the steps of:
   (a) passing the liquid through a P-removal bioreactor comprising an immobilized microbial consortia which are charged or recharged with a carbon source present in the liquid;
   (b) passing the effluent from step (a) through the P-removal bioreactor which has been charged or recharged from step (a) under conditions which allow the microbial consortia to uptake and store P compounds;
   (c) removing the wastewater from the P-removal bioreactor and providing a P-release solution effective to cause the microbial consortia to release the P previously stored; and
   (d) removing the P-release solution containing the released P from the P-removal bioreactor.

2. The process of claim 1 further comprising the step of passing the liquid through an anaerobic bioreactor comprising an immobilized microbial consortia which degrade organic components in the liquid and produce volatile fatty acids which serves as the carbon source.

3. The process of claim 2 further comprising the step of passing at least a portion of the effluent from the anaerobic bioreactor through a strictly anaerobic bioreactor comprising an immobilized methanogenic microbial consortia which metabolize the VFA's and produce methane.

4. The process of claim 3, wherein the effluent from the strictly anaerobic bioreactor is further treated to remove BOD and/or COD.

5. The process of claim 1 further comprising the step of passing the effluent from the P-removal bioreactor through at least one other bioreactor comprising an immobilized microbial consortia for at least partially removing N containing compounds, BOD and/or COD from the wastewater.

6. The process of claim 5 wherein the at least one other bioreactor comprises a nitrogen removal bioreactor comprising a denitrification zone comprising microbial consortia which convert nitrogen oxides into nitrogen gas and a nitrification zone comprising microbial consortia which convert ammonia into nitrogen oxides.

7. The process of claim 5 wherein the at least one other bioreactor further comprises an aerobic BOD removal bioreactor.

8. The process of claim 5 wherein the at least one other bioreactor further comprises an aerobic polishing bioreactor wherein residual ammonia and/or suspended solids are further polished out.

9. The process of claim 5 wherein there are at least two P-removal bioreactors used alternately such that while one is being charged or recharged with effluent from the anaerobic bioreactor, one other is being used to treat effluent from the nitrogen removal bioreactor.

10. The process of claim 9 wherein there are three P-removal bioreactors used alternately in a continuous fashion such that while one is being charged or recharged with effluent from the anaerobic bioreactor, a second is being used to treat effluent from the nitrogen removal bioreactor and the third is being treated with the P-release agent.

11. The process of claim 1 wherein step (b) is carried out under vigorous aerobic conditions.

12. The process of claim 11 wherein the dissolved oxygen level is greater than about 2 mg/l.

13. The process of claim 12 wherein the dissolved oxygen level is between about 3 to about 4 mg/l.

14. The process of claim 1 wherein the P-release solution comprises a solution of a suitable surfactant and a carbon source.

15. The process of claim 14 wherein the surfactant is Tween 20 and the carbon source of the P-release solution comprises volatile fatty acids.

16. A process of treating wastewater containing biodegradable suspended solids and/or organic compounds, said process comprising the steps of:
   (a) passing the wastewater through a facultative anaerobic bioreactor comprising a microbial consortia which produces hydrolyzing enzymes which breakdown the solids and/or organic compounds in the wastewater and which produce volatile fatty acids as a result of facultative anaerobic processes; and
   (b) passing at least a portion of the effluent from the facultative anaerobic bioreactor through a strictly anaerobic bioreactor comprising a methanogenic microbial consortia; and
   (c) wherein the effluent from the strictly anaerobic bioreactor is further treated to remove one of or a combination of any of the following: P-containing compounds, N-containing compounds, BOD, COD and/or suspended solids; and lie effluent from the strictly anaerobic bioreactor is further treated in one or both of: (i) an aerobic BOD removal bioreactor; or (ii) an aerobic polishing bioreactor where residual ammonia is oxidized to nitrogen oxides and where residual suspended solids are retained and degraded.

17. The process of claim 16 wherein there is no step of settling and removing solids from the wastewater prior to step (a).

18. The process of claim 16 wherein the microbial consortia in the facultative anaerobic bioreactor degrade complex P-containing compounds and N-containing compounds to simpler P-containing compounds and N-containing compounds.

19. The process of claim 16 wherein the methane produced in the strictly anaerobic bioreactor is removed and collected.

* * * * *